United States Patent [19]

Dopp

[11] 4,299,593
[45] Nov. 10, 1981

[54] METHOD AND APPARATUS FOR DETECTING AND MEASURING A GAS

[75] Inventor: Robert B. Dopp, Madison, Wis.

[73] Assignee: The Upjohn Company, Kalamazoo, Mich.

[21] Appl. No.: 31,990

[22] Filed: Apr. 20, 1979

[51] Int. Cl.³ .......................................... G01N 21/78
[52] U.S. Cl. .............................. 23/232 R; 23/230 A; 23/230 M; 422/91
[58] Field of Search ............ 23/230 A, 230 M, 232 R; 422/88, 106, 86, 90-92; 261/112

[56] References Cited

U.S. PATENT DOCUMENTS

| | | | |
|---|---|---|---|
| 2,116,999 | 5/1938 | Ashby | 261/112 |
| 2,356,530 | 8/1944 | Pflock | 261/112 |
| 2,534,229 | 12/1950 | Carhart et al. | 23/232 R |
| 2,728,639 | 12/1955 | McConnaughey | 23/232 R |
| 2,829,032 | 4/1958 | Barley et al. | 422/86 |
| 3,028,224 | 4/1962 | Ferrari | 23/232 R |
| 3,666,419 | 5/1972 | Cahour et al. | 23/230 A |
| 3,708,265 | 1/1973 | Lyshkow | 422/91 |
| 4,079,293 | 2/1978 | Grill et al. | 23/230 A |

FOREIGN PATENT DOCUMENTS 834816  5/1960  United Kingdom .................. 422/86

OTHER PUBLICATIONS

Reilly, D. A. "The Analysis of Combustion Gases: Development of a Continuous Analyzer for Hydrogen Cyanide" ICI Report. No. 82392 (2-76).
Buckley, P. S., *Techniques of Process Control*, John Wiley and Sons, Inc., New York, 1964, pp. 187.

*Primary Examiner*—William F. Smith
*Attorney, Agent, or Firm*—St. Onge, Steward, Johnston, Reens & Noë

[57] ABSTRACT

A technique is described for continuously detecting or measuring a gas such as hydrogen cyanide in a gas stream. The gas stream is passed in counterflow relationship with a well defined stream of gas absorbing reagent liquid in an absorption cell through which the reagent flows under gravity feed. The exposed reagent is passed through a heater in which the color of the reagent is developed. The reagent is passed through the heater at a constant regulated flow rate with a flow controller operative between the absorption cell and the heater to provide a consistent color development. A stable and consistent detection and measurement of the amount of hydrogen cyanide in the gas stream is obtained.

1 Claim, 2 Drawing Figures

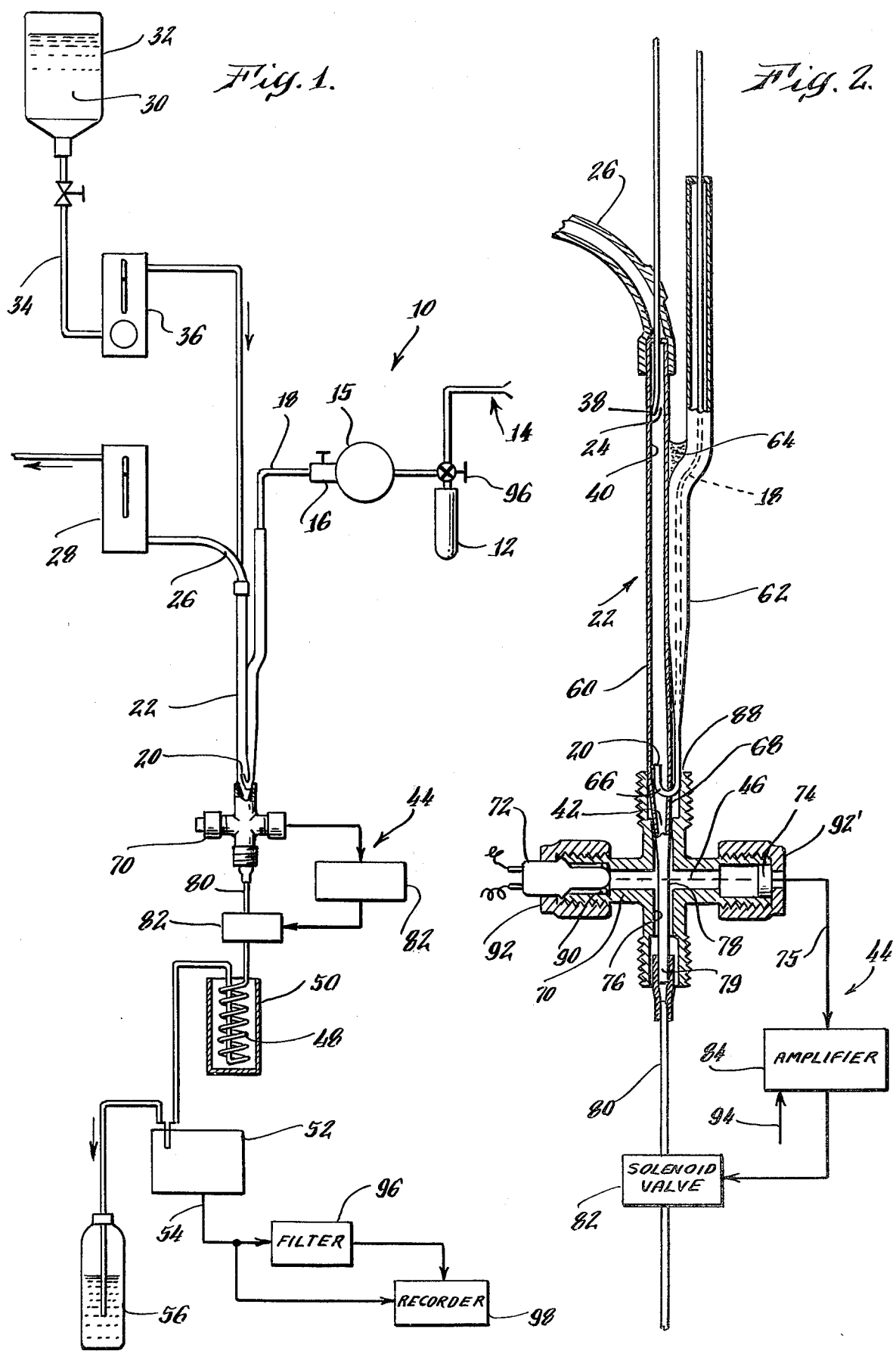

METHOD AND APPARATUS FOR DETECTING AND MEASURING A GAS

FIELD OF THE INVENTION

This invention relates to an apparatus and method for detecting and measuring the presence of a gas. More specifically, this invention relates to a method and apparatus for measuring the amount of hydrogen cyanide in a stream of gas.

BACKGROUND OF THE INVENTION

Techniques for analyzing the combustion of many materials for hydrogen cyanide have been described. In accordance with one such technique as described in a report by D. A. Reilly, a continuous analysis of combustion gas is made for hydrogen cyanide (HCN) to enable one to study the combustion of polyurethane foams and the like, (see a report entitled "The Analysis of Combustion Gases: Development of a Continuous Analyzer For Hydrogen Cyanide" by D. A. Reilly, ICI Report No. 82392, February 1976).

As described in the aforementioned report, a gas stream containing hydrogen cyanide is passed through an absorption cell through which a hydrogen cyanide absorbing liquid reagent such as an alkaline aqueous solution of sodium picrate is passed. The exposed sodium picrate reagent with any absorbed hydrogen cyanide is subsequently heated to develop a color. The density of the color of the reagent is determined in a spectrophotometer to determine and measure the absorbed hydrogen cyanide.

Although the described technique detects and measures the presence of hydrogen cyanide in a continuous manner, the technique as described has a slow response time and tends to exhibit undesirable fluctuations.

SUMMARY OF THE INVENTION

With a technique for detecting and measuring a gas such as hydrogen cyanide with an apparatus and method in accordance with the invention, a rapid and stable gas analysis can be made.

As described herein for one technique in accordance with the invention for detecting and measuring the hydrogen cyanide in a stream of gas, the latter is passed in counterflow relationship with a flow of gas absorbing liquid reagent flowing under gravity in a well defined stream along an inner wall of an absorption cell.

The absorption cell is made with a small volume to provide a relatively high reagent surface area for contact with the gas stream and a short flush time. The flow of reagent through the absorption cell is controlled commensurate with desired sensitivity and response to provide a consistent absorption of hydrogen cyanide.

Downstream of the absorption cell, the flow of reagent liquid is precisely controlled with a flow controller which operates to establish a consistent flow of reagent through a subsequent modifier in which a characteristic of the liquid reagent, such as its color as a result of absorbed hydrogen cyanide is developed. An instrument, such as a spectrophotometer, is then used, to optically detect and measure the color characteristic of the liquid reagent and provide a signal representative of the magnitude of the characteristic. In the embodiment, the amount of hydrogen cyanide in the gas stream is measured.

As described herein for a preferred embodiment, the controller maintains a meniscus of the gas absorbing liquid reagent at a desired location relative to a subsequent reagent heater. This enables the flow of reagent to be substantially constant throughout the heater and enables a consistent color reading from the color detector.

With a gas detection and measuring technique in accordance with the invention, cyanide can be continuously detected and measured with a rapid response and with consistent and accurate results. It is, therefore, an object of the invention to provide a gas detection and measuring method and apparatus having these advantageous features and particularly useful in the detection or measuring of a cyanide gas such as hydrogen cyanide.

BRIEF DESCRIPTION OF DRAWINGS

These and other advantages and objects of the invention can be understood from the following description of an embodiment described in conjunction with the following drawings.

FIG. 1 is a view in elevation and in partial section of an apparatus in accordance with the invention for detecting and measuring a gas such as hydrogen cyanide.

FIG. 2 is an enlarged sectional view in elevation of a gas absorption cell and gas absorbing liquid reagent flow controller used in the apparatus of FIG. 1

DETAILED DESCRIPTION OF EMBODIMENT

With reference to FIGS. 1 and 2, a gas detection and measuring apparatus 10 is shown. A gas from a source such as a container 12 or sampling station 14 at a combustion site where a material is burned, is applied under pressure such as by a pump 15 through a valve 16, intake conduit 18 to a bottom located intake 20 of a vertically oriented gas absorption cell 22. The gas passes upwardly through absorption cell 22 to a discharge 24 and through a conduit 26 and a gas flow meter and control 28 to a suitable atmospheric exhaust or receptacle (not shown).

A gas absorbing liquid reagent 30 is provided from a reservoir 32 and applied by way of a gravity feed through a conduit 34 and a liquid flow meter and valve control 36 to a liquid reagent inlet 38 at the upper end of absorption cell 22. The gas absorbing liquid is, as shown in FIG. 2, applied in close proximity to the inner wall 40 of absorption cell 22 to flow in a well defined film or stream along wall 40 down to an outlet 42.

A liquid flow control 44 is provided whereby the absorbing liquid is maintained at a level 46 which is at a predetermined distance above a reagent heater 50 located below absorption cell 22. The heater 50 acts as a modifier of a characteristic of liquid reagent whereby, for example, its color as a result of the absorption of hydrogen cyanide is developed. By carefully maintaining a steady flow of the liquid reagent from a point above heater 50, the latter can develop the color due to the presence of hydrogen cyanide in a consistent manner.

The reagent liquid flows through a coil 48 which is submerged in a heated bath in a heater 50 to raise the temperature of the liquid reagent to a temperature where absorbed cyanide alters the color of the liquid reagent. The heated liquid reagent is then passed through an instrument such as a spectrophotometer 52 which is sensitive to the color change developed in heater 50. Instrument 52 produces a signal on line 54 indicative of the magnitude of the developed characteristic of the liquid reagent, i.e. the optical transmissivity, %T, at a characteristic color wavelength of the heated liquid reagent. This optical transmission measurement may then be transformed to an optical density, OD, measurement with the relationship OD=log (100/%T). The reagent is finally discharged in a waste receptacle 56. The signal on line 54 can be used to generate a warning and can be recorded on a visual or magnetic signal recorder.

The apparatus 10 is particularly effective in detection and measuring of a cyanide gas such as hydrogen cyanide. In such case, the liquid reagent 30 as described in the aforementioned D. A. Reilly article may be an aqueous solution of sodium picrate. The sodium picrate may be drawn from reservoir 32 as shown or siphoned off as long as an even, smooth flow through absorption cell 22 is obtained.

The absorption cell 22 is, as shown in FIG. 2, formed of a pair of glass tubes such as pipettes 60, 62 which are joined as shown with a suitable adhesive 64 formed of epoxy cement. Pipette 62 has one end 66 bent into a U shape terminating at intake 20. Pipette 60 has an opening 68 blown into it at the place where the cross-section of pipette 60 begins to reduce. The opening 68 is made sufficiently large to enable end 66 to fit through after which space around end 66 and at opening 68 is sealed.

The joined pipettes 60, 62 fit into a fluid level monitor 70 which has a light sensitive optical path coincident with the desired level 46 for the sodium picrate solution. The fluid level monitor 70 includes a light source 72 and a photo cell 74 which is oriented to sense changes in the optical path 46 and produce a signal indicative thereof on output line 75.

The pipette 60 has its lower end extend into a through bore 76 of fluid level monitor 70 and preferably has a section 78 opposite the optical path 46 flattened to facilitate the observation of optical transmission changes caused by variations in the level of the gas absorbing liquid reagent in section 78. The absorption cell 22 is carefully seated in the fluid level monitor 70 and may be supported with other conventional brackets.

The lower end 79 of the absorption cell 22 connects to a flexible conduit 80 which passes through a solenoid driven pinch valve 82 which is so located that a relatively smooth and constant flow of liquid reagent is obtained through heater 50. An amplifier 84 interconnects the output line 75 to solenoid valve 82 in such manner that the presence of liquid reagent in the optical path 46 opens the valve 82 and the absence of the liquid reagent closes the valve 82. With such control, a meniscus of the liquid reagent can be maintained at the level 46, so as to in effect provide a constant head of liquid reagent above the heater 50 and precisely control the travel time of the reagent in heater 50.

The fluid level monitor 70 may be formed from a conventional metal housing for a four-way conduit connector which is modified with a notch 88 to receive section 66 of pipette 62. A ferrule 90 is provided to seat lamp 72 which is retained by a nut 92. The photocell 74 is similarly retained by a nut 92'.

In the operation of apparatus 10, the hydrogen cyanide absorbing reagent liquid 30 is prepared as described in the Reilly report, mixed and filtered, which can be done at elevated temperature if mixing time is to be reduced.

The temperature of the bath in heater 50 is kept constant by wrapping it in a heating tape and insulating it. The bath temperature is maintained about 90° C. with a suitable controller and a glass exchanger coil 48 of a length of about 22 inches as suggested in the Reilly report is used.

The apparatus 10 is arranged as illustrated in a vertical manner so that the reagent liquid 30 can flow under gravity in a smooth manner throughout. Small i.d. tubing is used, such as of the order of 0.030 inch i.d. teflon tubing with junctions to be constructed for reduced dead volumes. The absorption cell 22 should, before use, be thoroughly cleaned to remove all dirt and allow a smooth flow of reagent liquid. Cleaning can be done by soaking in chromic acid for a minute followed by thorough rising with distilled water without drying. The reagent liquid is allowed to flow through the apparatus for several minutes to remove any crystals that may have grown in the various conduits. Such continuous flow is obtained by adjusting an offset control 94 on amplifier 84 as a result of which the solenoid valve 82 can be kept open. Cleanliness of the absorption cell 22 can be observed from the presence of a single column of reagent liquid flowing down wall 40 of pipette 60.

The proper setting for the solenoid valve 82 can be obtained by altering off-set control 94 on amplifier 84 until a position is reached where the valve 82 opens and closes. The desired flow rate for the sodium picrate reagent 30 is then set by adjusting the flow measuring and control 36. A high flow rate produces a faster response time, greater dynamic range through reducing sensitivity. The selected flow range thus may vary, depending upon the required sensitivity, range and response characteristics.

The apparatus 10 is calibrated by feeding a span gas through absorption cell 22 with a known concentration of hydrogen cyanide. Such span gas may be obtained from a container 12, though care should be taken to periodically verify the level of concentration of hydrogen cyanide in the span gas since this is a strong reducing agent and may react with the wall of container 12. Such verification may be made by passing a known volume of hydrogen cyanide through a scrubber containing a known weight of sodium picrate reagent solution. The solution is then collected and heated to 90° C. for a sufficiently long period, say 30 minutes, for a full color development and analysis by a spectrophotometer. At the same time, a standard cyanide solution, having a concentration of CN$^-$ of 5 ppm in sodium picrate solution and a blank of the same batch of sodium picrate solution are prepared and heated in separate tubes. After a cooling period, of for example 30 minutes, the color in these tubes is read in a colorimeter for which the blank represents minimum opacity or 100% T.

Since the optical density (log of 100/%T) varies linearly with respect to the concentration of cyanide, the CN$^-$ concentration C, in the exposed sodium picrate solution is determined by the relationship $$C = \frac{\log\left[\frac{100}{\%T} \text{ of unknown}\right]}{\log\left[\frac{100}{\%T} \text{ of standard}\right]} \times \text{Concentration of Standard (5 ppm)}$$

where %T is the percentage of light being transmitted through the exposed solution.

The concentration, ppm, of the hydrogen cyanide, |HCN| in the span gas may then be derived by the relationship $$[HCN] \text{ span gas} = \frac{C \times W \times t}{P \times V} \times 2396.7$$

where W represents grams of sodium picrate solution in the scrubber, t is the ambient temperature in °K, P is the barometric pressure in mm Hg, and V represents the amount of span gas used in the calibration procedure or bubbled through cell 22 in cubic centimeters.

Calibration of the apparatus 10 may then be carried out by feeding the span gas from container 12 through the absorption cell 22 at one rate and using a flow rate for the sodium picrate reagent liquid selected to yield reasonably fast response time while also yielding a useful dynamic range over which different hydrogen cyanide concentrations can be measured.

For example, a span gas flow of 125 cc/minute and sodium picrate reagent liquid flow of 2.3 cc/minute provided a useful dynamic range, where 660 ppm of HCN yielded a spectrometer reading of 16% of T with a response of about 24 seconds to 90% of this spectrometer reading and 45 seconds to its full valve of 16%T.

Hence, using the span gas for which the concentration C in ppm of HCN has been determined and with the gas flow rates and sodium picrate reagent flow rates selected, the resulting spectrometer reading is used for calibrating subsequent measurements in accordance with the following relationship.

$$\text{HCN ppm of unknown} = \frac{\log \frac{100}{\% T} \text{ unknown}}{\log \frac{100}{\% T} \text{ span}} \times C \text{ of span gas}$$

Once apparatus 10 has been calibrated for the gas flow rate setting, as determined by flow control 28, and the gas absorbing reagent liquid flow rate as set by flow control 36, a valve 96 is switched to allow gas from a site 14 to be analyzed for HNC concentration.

The exposed sodium picrate reagent develops a color depending upon time and temperature. A high flow rate of the reagent reduces color development unless higher HCN concentrations are present. In such case a higher range of HNC concentrations can be detected and measured. With a lower flow rate for liquid reagent, the apparatus 10 correspondingly responds with greater sensitivity to sense and measure smaller HCN concentrations.

The color development of the exposed sodium picrate reagent liquid can be accelerated by increasing the temperature of heater 50. However, since air bubbles are already being driven out of an aqueous solution at 90° C. and interfere with the detection of HCN in spectrometer 52, further temperature increases are normally undesirable. One could employ a bubble remover; however, this would tend to obscure the detection and measurement of hydrogen cyanide as well.

The presence of air bubbles in the reagent liquid causes spikes to be generated on output 54 of spectrometer 52. Such spikes may be electrically filtered out with a filter 96 in light of the substantial difference in time duration of spikes produced by air bubbles and responses due to the presence of hydrogen cyanide. The output of spectrometer 52 and filter output may be recorded on recorder 98.

The use of gravity feed for the gas absorbing reagent liquid contributes significantly to the stability and consistency of the operation of the apparatus 10. The steady flow of the reagent liquid in the absorption cell 22 enables a precise equilibrium between the liquid and gas flows in the cell, particularly when the flows are countercurrent.

The liquid flow control 44 provides a precise head pressure for the exposed reagent liquid prior to its passage through the heater 50 and spectrometer 52. As a result, the exposed reagent liquid has a well controlled duration in heater 50 so that the reagent temperature upon entering spectrometer 52 is consistently the same. In establishing a fixed reagent liquid head and thus consistent reagent flow through heater 50 and spectrometer 52, care should be taken to avoid focusing control on an air bubble in section 78 of pipette 60. This can be quickly detected, however, by observing the resulting back-up of reagent into absorption cell 22.

Having thus explained an apparatus for the detection and measuring of hydrogen cyanide in a continuous manner, the advantages of the invention can be appreciated. Variations from the described embodiment can be implemented by one skilled in the art without departing from the scope of the invention as determined by the following claims.

What is claimed is:

1. In a method for measuring the amount of hydrogen cyanide in a gas stream by utilizing a hydrogen cyanide absorbing reagent liquid, which upon exposure to and absorption of hydrogen cyanide, undergoes a color change upon passage of the exposed reagent liquid through a heater for subsequent analysis of the reagent liquid in a color detector, the improvement comprising the steps of:

passing the stream of gas in counter flow relationship with a flow of hydrogen cyanide absorbing reagent liquid for exposure to and absorption by the latter of hydrogen cyanide while feeding the reagent liquid under gravity in a well defined stream;

controlling the flow rate of said exposed reagent liquid at a point subsequent to its exposure to hydrogen cyanide and prior to the entry of the reagent to the heater with a predetermined head of the reagent liquid above said heater by optically sensing the reagent liquid at a predetermined level above said heater; and varying the flow of said reagent liquid at a place above said heater to maintain a meniscus of the reagent liquid at said predetermined level thereby establishing through said heater a substantially constant flow rate for a consistent measurement of the color of said exposed reagent liquid.

* * * * *